United States Patent [19]

Ansmann et al.

[11] Patent Number: 5,439,671
[45] Date of Patent: Aug. 8, 1995

[54] PROCESS FOR THE PRODUCTION OF NEUTRAL-TASTING PASTES OF ALKYL ETHER SULFATES IN GLYCEROL

[75] Inventors: Achim Ansmann, Erkrath; Willi Breitzke, Duesseldorf; Karl-Heinz Gantke, Moenchengladbach, all of Germany

[73] Assignee: Henkel Kommanditgesellschaft auf Aktien, Duesseldorf, Germany

[21] Appl. No.: 211,073

[22] PCT Filed: Sep. 8, 1992

[86] PCT No.: PCT/EP92/02073

§ 371 Date: Mar. 18, 1994

§ 102(e) Date: Mar. 18, 1994

[87] PCT Pub. No.: WO93/06081

PCT Pub. Date: Apr. 1, 1993

[30] Foreign Application Priority Data

Sep. 19, 1991 [DE] Germany .................. 41 31 118.3

[51] Int. Cl.$^6$ .............................................. A61K 7/16
[52] U.S. Cl. ...................................... 424/56; 252/332;
252/353; 424/401; 562/110; 562/36
[58] Field of Search ................ 562/110, 36; 252/332,
252/353; 424/56, 401

[56] References Cited

U.S. PATENT DOCUMENTS

| | | | |
|---|---|---|---|
| 3,893,940 | 7/1975 | Ohogoshi et al. | 252/353 |
| 4,411,815 | 10/1983 | Ando et al. | 252/353 |
| 5,362,479 | 8/1994 | Breitzke et al. | 424/56 |

FOREIGN PATENT DOCUMENTS

| | | |
|---|---|---|
| 0052801 | 6/1982 | European Pat. Off. . |
| 2253896 | 5/1973 | Germany . |
| 3126175 | 4/1982 | Germany . |
| 3044488 | 7/1982 | Germany . |
| 3447867 | 7/1986 | Germany . |
| 3503331 | 8/1986 | Germany . |

OTHER PUBLICATIONS

Soap/Cosmetics/Chemical Spec. for Jan. 1988, p. 34.

*Primary Examiner*—Glennon H. Hollrah
*Assistant Examiner*—Scott C. Rand
*Attorney, Agent, or Firm*—Wayne C. Jaeschke; John E. Drach; Henry E. Millson, Jr.

[57] ABSTRACT

Process for the production of a neutral-tasting paste of an alkyl ether sulfate in glycerol, comprising the steps of:

A) forming an aqueous paste of at least one alkyl ether sulfate wherein the aqueous paste contains from about 25 to about 75% by weight of alkyl ether sulfate;

B) adding glycerol to the aqueous paste from step A) in from about 1 to about 4 times the quantity by weight of the aqueous paste;

C) distilling off substantially all of the water present in the mixture resulting from step B) to produce a substantially ambydrous paste; and D) passing steam heated to a temperature above 100° C. through skid paste with intensive whirling of the paste and steam phases.

9 Claims, No Drawings

PROCESS FOR THE PRODUCTION OF NEUTRAL-TASTING PASTES OF ALKYL ETHER SULFATES IN GLYCEROL this application is a 371 of PCT/EP92/02073, filed Sep. 8, 1992.

BACKGROUND OF THE INVENTION

1. Field of the Invention

This invention relates to a process for the production of neutral-tasting pastes of alkyl ether sulfates in glycerol.

2. Statement of Related Art

In contrast to alkyl sulfates, alkyl ether sulfates have hardly ever been used in toothpastes on account of their unpleasant taste and aftertaste.

It is known from German patent application DE 30 44 481 that 1,4-dioxane can be removed from water-containing pastes of alkyl ether sulfates in admixture with water by azeotropic evaporation. DE-OS 34 47 867 describes a process for the removal of 1,4-dioxane from alkyl ether sulfates, in which an ethoxylated silicone oil is added to the water-containing surfactant paste for defoaming purposes and steam is subsequently passed through the resulting mixture. These processes give water-containing pastes of alkyl ether sulfates which, by virtue of their reduced 1,4-dioxane content and the lower danger potential resulting therefrom, may be used with advantage in detergents and cleaning preparations.

However, distillation-based operations involving water-containing alkyl ether sulfate pastes of relatively high concentration are complicated by the presence of gel phases. Accordingly, there is a need for processes which enable unwanted secondary products to be removed from alkyl ether sulfate pastes. These secondary products are only present in low concentrations and, as in the case of taste-forming or odor-emitting substances for example, are generally not known in their entirety.

DESCRIPTION OF THE INVENTION

The problem addressed by the present invention was to provide a process for the production of neutral-tasting pastes of alkyl ether sulfates.

According to the invention, this problem has been solved by a process for the production of neutral-tasting pastes of alkyl ether sulfates in glycerol, in which (a) glycerol is added to an aqueous paste containing 25 to 75% by weight of an alkyl ether sulfate in a 1-to 4-fold excess by weight, based on the aqueous alkyl ether sulfate paste, and the water present is distilled off substantially completely from the mixture at elevated temperature and (b) steam heated to temperatures above 100° C. is passed through the mixture obtained in this way with intensive whirling of the liquid and steam phases.

In the context of the invention alkyl ether sulfates are the sulfates of adducts of ethylene oxide (EO) and/or propylene oxide (PO) with saturated and/or unsaturated, linear and/or branched fatty alcohols obtainable by known methods. The fatty alcohols on which the alkyl ether sulfates are based may be pure compounds. However, it is normally preferred to use mixtures of different fatty alcohols obtained from native raw materials, such as fats and oils. These fatty alcohols may be reacted with the alkylene oxides, for example under pressure and in the presence of catalysts, to form fatty alcohol alkoxylates.

It may stated with regard to the degree of alkoxylation that alkoxylation reactions such as, for example, the addition of x moles of ethylene oxide onto 1 mole of fatty alcohol by known methods of ethoxylation do not give an adduct per se, but rather a mixture of residues of free fatty alcohol and a number of homologous (oligomeric) addition products of 1, 2, 3, ... x, x+1, x+2 ... etc. molecules of ethylene oxide per molecule of fatty alcohol. The average degree of ethoxylation (x) is defined by the starting quantities of fatty alcohol and ethylene oxide. The distribution curve of the homolog mixture generally shows a maximum in the range from x−3 to x+3. Further information on this subject can be found, for example, in the Journal Soap/Cosmetics/Chemical Specialties, Jan. 1988, page 34.

The desired alkyl ether sulfates are ultimately obtained by reaction of the fatty alcohol alkoxylates with, for example, sulfur trioxide or chlorosulfonic acid and subsequent neutralization, for example with alkali metal, alkaline earth metal, aluminium or ammonium hydroxides.

Preferred alkyl ether sulfates are compounds corresponding to formula (I):

$$R-O-(C_nH_{2n}O)_x-SO_3M \qquad (I)$$

in which R is a saturated or olefinically unsaturated, linear or branched $C_{8-22}$ alkyl radical, n is the number 2 or 3, x is a number of 1 to 15 and M is hydrogen, an alkali metal, an alkaline earth metal, aluminium, an ammonium group or an alkyl or alkylol ammonium group containing 1 to 4 carbon atoms in each alkyl or alkylol group.

Particularly preferred compounds are those in which R is a saturated $C_{8-16}$ alkyl radical, n=2, x is a number of about 2 to 10 and M is sodium, potassium, magnesium, aluminium, ammonium or a mono-, di- or triethanolammonium group.

Step (a) of the process according to the invention is carried out using in particular aqueous pastes containing 30 to 70% by weight and preferably 55 to 70% by weight of an alkyl ether sulfate.

The pastes of alkyl ether sulfates in glycerol obtained by the process according to the invention still contain water from the steam treatment and may be used as such. However, it may be desirable to reduce their water content, for example by distillation. For practical reasons, water contents below 3% by weight have proved to be favorable.

The neutral-tasting pastes of alkyl ether sulfates in glycerol according to the present invention are suitable for use in the cosmetics field. Thus, cosmetic preparations where it is important to avoid any adverse effect on taste, for example toothpastes, can be produced on the basis of the pastes according to the invention.

The following Examples are intended to illustrate the invention without limiting in any way.

EXAMPLES

1. Substances used
   Texapon N 70: aqueous solution of sodium lauryl ether sulfate; active substance content: approx. 70% by weight ("Texapon®N70"; Henkel KGaA, Düsseldorf)
   Glycerol: 99% (Henkel KGaA, Düsseldorf)

Dehydazol A 400 P: carboxymethyl cellulose, Na salt (Henkel KGaA)
Sident 12 DS: silica, precipitated (Degussa AG)
Syloblanc 34 (Sn 34): silica, amorphous (Grace)

Example 1

A mixture of 100 g of Texapon N70 and 400 g of glycerol was introduced into a stirred vessel and the water present therein was removed by distillation first at 80° C./100 torr and then at 110° C./20 torr. Steam was then passed through the paste obtained for 2.5 hours at 120° C./12 torr, followed by drying for 30 minutes at 120° C./5 torr. The water content of the resulting paste of Texapon N 70 in glycerol was 0.3% by weight.

Example 2

Toothpaste formulations A and B (see Table 1) were prepared to test the taste properties of the alkyl ether sulfate produced by the process according to the invention in comparison with the corresponding untreated alkyl ether sulfate.

TABLE 1

| Constituent | Formulation A % by weight | Formulation B % by weight |
| --- | --- | --- |
| Dehydazol A 400 P | 1.2 | 1.2 |
| Sident 12 DS | 21.0 | 21.0 |
| Syloblanc 34 (Sn 34) | 1.0 | 1.0 |
| Glycerol 86% | 25.0 | 25.0 |
| Sorbitol 70% | 15.0 | 15.0 |
| NaF | 0.22 | 0.22 |
| Saccharin Na | 0.1 | 0.1 |
| Flavoring oil | 1.0 | 1.0 |
| TiO$_2$ | 1.0 | 1.0 |
| Preservative | 0.1 | 0.1 |
| Texapon N70$^{a)}$ (acc. to Example 1) | 2.0 | — |
| Texapon N70$^{a)}$ (untreated) | — | 2.0 |
| Water, dist. | ad 100 | ad 100 |

$^{a)}$In % by weight of active substance

Result:

Formulation A which contained alkyl ether sulfate pretreated by the process according to the invention was substantially neutral in its taste while formulation B which contained the untreated alkyl ether sulfate had a pronounced taste and aftertaste.

We claim:

1. A process for the production of a neutral-tasting paste of an alkyl ether sulfate in glycerol, comprising the steps of:
   A) forming an aqueous paste of at least one alkyl ether sulfate wherein the aqueous paste contains from about 25 to about 75% by weight of alkyl ether sulfate;
   B) adding glycerol to the aqueous paste from step A) in from about 1 to about 4 times the quantity by weight of the aqueous paste;
   C) distilling off substantially all of the water present in the mixture resulting from step B) to produce a substantially anhydrous paste; and
   D) passing steam heated to a temperature above 100° C. through said paste with intensive whirling of the paste and steam phases.

2. The process of claim 1 wherein in step A) the aqueous paste contains from about 30 to about 70% by weight of alkyl ether sulfate.

3. The process of claim 2 wherein the aqueous paste contains from about 55 to about 70% by weight of alkyl ether sulfate.

4. The process of claim 1 wherein the at least one alkyl ether sulfate in step A) is derived from a mixture of fatty alcohols obtained from a native fat or oil.

5. The process of claim 1 wherein the at least one alkyl ether sulfate in step A) is at least one alkyl ether sulfate of, the formula:

$$R-O-(C_nH_{2n}O)_x-SO_3M \qquad (I)$$

in which R is a saturated or olefinically unsaturated, linear or branched C$_{8-22}$ alkyl radical, n is the number 2 or 3, x is a number of from about 1 to about 15, and M is hydrogen, an alkali metal, an alkaline earth metal, aluminum, an ammonium group or an alkyl or alkylol ammonium group containing 1 to 4 carbon atoms in each alkyl or alkylol group.

6. The process of claim 5 wherein in the alkyl ether sulfate of formula I, R is a saturated C$_{8-16}$ alkyl radical, n=2, x is a number of from about 2 to about 10, and M is sodium, potassium, magnesium, aluminum, ammonium or a mono-, di- or triethanolammonium group.

7. The process of claim 1 wherein following step D) water is removed from the paste until the paste has a water content of less than 3% by weight.

8. A toothpaste composition containing a surfactant effective quantity of the neutral-tasting paste prepared by the process of claim 1.

9. A toothpaste composition containing a surfactant effective quantity of the neutral-tasting paste prepared by the process of claim 5.

* * * * *